United States Patent
Moritz et al.

(10) Patent No.: US 11,024,492 B2
(45) Date of Patent: Jun. 1, 2021

(54) METHOD TO OBTAIN UNBIASED IDENTIFICATION OF INTERACTION OF TEST COMPOUNDS WITH THE PROTEOME

(71) Applicant: Institute for Systems Biology, Seattle, WA (US)

(72) Inventors: Robert L. Moritz, Seattle, WA (US); Samuel Bader, Seattle, WA (US); Ulrike Kusebauch, Seattle, WA (US)

(73) Assignee: Institute for Systems Biology, Seattle, WA (US)

( * ) Notice: Subject to any disclaimer, the term of this patent is extended or adjusted under 35 U.S.C. 154(b) by 782 days.

(21) Appl. No.: 15/202,378

(22) Filed: Jul. 5, 2016

(65) Prior Publication Data

US 2017/0010229 A1    Jan. 12, 2017

Related U.S. Application Data

(60) Provisional application No. 62/189,665, filed on Jul. 7, 2015.

(51) Int. Cl.
*G01N 33/48* (2006.01)
*H01J 49/00* (2006.01)
*G01N 33/68* (2006.01)
*G06G 7/58* (2006.01)

(52) U.S. Cl.
CPC ...... *H01J 49/0036* (2013.01); *G01N 33/6848* (2013.01); *G01N 2500/04* (2013.01); *G01N 2570/00* (2013.01)

(58) Field of Classification Search
None
See application file for complete search history.

(56) References Cited

U.S. PATENT DOCUMENTS

| 8,969,014 | B2 | 3/2015 | Nordlund |
| 2006/0008851 | A1 | 1/2006 | Aebersold et al. |
| 2013/0206979 | A1 | 8/2013 | Bonner et al. |
| 2014/0057368 | A1 | 2/2014 | Nordlund |
| 2015/0160234 | A1 | 6/2015 | Goodlett |

OTHER PUBLICATIONS

Deutsch et al., "PeptideAtlas: a resource for target selection for emerging targeted proteomics workflows," EMBO Rep (2008) 9(5):429-434.
Farrah et al., "PASSEL: the PeptideAtlas SRM experiment library," Proteomics (2012) 12(8):1170-1175.
International Search Report and Written Opinion for PCT/US2016/041188, dated Oct. 6, 2016.
Jafari et al., "The cellular thermal shift assay for evaluating drug target interactions in cells," Nat Protoc (2014) 9(9):2100-2122.
Kusebauch et al., "Using PeptideAtlas, SRMAtlas, and PASSEL: Comprehensive Resources for Discovery and Targeted Proteomics," Curr Protoc Bioinformatics (2014) 46:13.25.1-28.
Liu et al., "Quantitative measurements of N-linked glycoproteins in human plasma by SWATH-MS," Proteomics (2013) 13(8):1247-1256.
Molina et al., "Monitoring drug target engagement in cells and tissues using the cellular thermal shift assay," Science (2013) 341(6141):84-87.
Picotti et al., "A database of mass spectrometric assays for the yeast proteome," Nat Methods (2008) 5(11):913-914.

*Primary Examiner* — Eric S Dejong (74) *Attorney, Agent, or Firm* — Morrison & Foerster LLP (57) ABSTRACT

The invention provides an unbiased method to assess the binding of a test compound to a multiplicity of proteins in the same sample, including samples from living cells by applying the unbiased determination technique of SWATH-MS or the biased technique of SRM-MS to a thermal shift assay to evaluate drug target interactions. In addition, the results created by SWATH-MS can be analyzed by SRM-MS in a biased manner to assess the binding of a test compound to a multiplicity of proteins in the same sample, including samples from living cells.

10 Claims, 4 Drawing Sheets

METHOD TO OBTAIN UNBIASED IDENTIFICATION OF INTERACTION OF TEST COMPOUNDS WITH THE PROTEOME

CROSS-REFERENCE TO RELATED APPLICATION

This application claims priority from U.S. provisional application 62/189,665 filed 7 Jul. 2015, the contents of which is incorporated herein by reference in its entirety.

TECHNICAL FIELD

The invention is in the field of drug discovery, mainly, but more generally is directed to improvements in identifying interactions of compounds with proteins in complex mixtures where the results are unbiased and not determined by preconceived notions of binding characteristics. The invention takes advantage of an established technique for surveying the protein composition of a complex sample with a method for determining interaction of proteins with test compounds by assessing solubility variation with temperature.

BACKGROUND ART

Methods are available to assess the interaction of a compound with a protein by observing the effect of the compound on solubility of the protein. A formal embodiment of this technique is referred to as a thermal shift assay which is described in detail by Nordlund in US2014/0057368, now U.S. Pat. No. 8,969,014, and its use in evaluating drug target interactions in particular is described by Jafari, R., et al., *Nature Protocols* (2014) 9:2100-2122. In this assay, the effect of the compound on the solubility of a target protein is observed as a function of temperature. The assay is based on the principle that coupling the compound to the protein stabilizes the protein changes its solubility at temperatures where otherwise the protein would be precipitated. Thus, in general, the test involves contacting a sample containing a target protein whose interaction with the compound is to be evaluated with the compound and subjecting resulting mixture to a series of different temperatures including a temperature that is differential from than the original precipitation or melting temperature of the target protein, separating soluble from insoluble protein and analyzing one or both of the resulting fractions for protein concentration. Heretofore, a typical analysis would employ Western blotting using target protein specific affinity reagents as the readout for analysis. See, for example, Martinez-Molina, M. D., et al., *Science* (2013) 341:84-87.

An alternative method to assess the quantity of protein in the soluble or insoluble fraction is the use of "shotgun" mass spectrometry. In this method, the mass spectrometer is either instructed to focus on the fragmentation of the most concentrated protein in the sample or the mass spectrometer can be set to measure concentration of a particular protein identified by its molecular mass.

While Western blot theoretically could result in analyzing more than one protein in a sample, the method is cumbersome and limited by available affinity reagents and an upper limit in capacity of gels and detection levels. Shotgun mass spectrometry (MS), of course, biases the results by virtue of either the quantity of protein relative to other proteins in the sample or by a preconceived setting of the mass spectrometer providing stochastic measurements and ultimately limits the identification of these proteins.

The present invention overcomes the obstacles described above with respect to complex protein samples, including those extracted directly from living cells (or contained in living cells and later extracted) by employing a technique that results in an unbiased analysis of the concentration of every protein present in the sample regardless of its initial concentration or final concentration and without prior assumptions about which proteins will be most prevalent or will bind the test compound. This technique is known in the art as Sequential Windowed data independent Acquisition of the Total High resolution Mass Spectroscopy (SWATH-MS) which is described by Aebersold, R., in U.S. patent application 2006/0008851 and its various applications are described, for example, in Liu, Y., et al., *Proteomics* (2013) 13:1247-1256. Identification of parameters associated with various proteins have been described by Deutsch, E. W., et al., *EMBO Reports* (2008) 9:429-434 and by Farrah, T., et al., *Proteomics* (2012) 12:1170-1175.

Adapting the SWATH-MS technique to characterizing the results of proteome thermal shift assays has the highly desirable result of permitting simultaneous analysis of all of the proteins to which a compound is (or is not) bound along with a measure of the affinity of the binding. This enables identification not only of compounds that are successful in interacting with a desired target protein, but also assessing the possibility of side effects of a drug, for example, by viewing the interaction of a successful (or unsuccessful) test compound with alternative proteins where interaction is unknown or is not desired.

The present invention also utilizes a targeted identification and quantitation technique using the same predefined library used in SWATH-MS to specifically monitor proteins of interest, and any others up to a maximum of ~200 per analysis, with known or suspected interaction with the compound. This technique is known in the art as Selected Reaction Monitoring or Multiple Reaction Monitoring (abbreviated as SRM-MS or MRM-MS) which is described by Aebersold, R., in U.S. patent application 2013/30206979 and its various applications are described, for example, in Kusebauch, U., et al., *Curr. Protoc. Bioinformatics* (2014) 46:13.25.1-13.25.28. Identification of parameters associated with various proteins has been described by Picotti, P., et al., *Nat. Methods* (2008) 5:913-914.

DISCLOSURE OF THE INVENTION

In one aspect, the invention is directed to the application of a powerful tool—SWATH-MS—to assessment of interactions of test compounds with complex mixtures of proteins, including those representing the entire proteome of cells. The application of SWATH-MS to cellular thermal shift assays (CTSA) results in effective multiplexing over mixtures containing numerous proteins, including virtually entire proteomes from not only bacterial cells, but also mammalian cells. CTSA has been described in detail in the above cited paper by Martinez-Molina, *Science* (2013) as well as in U.S. Pat. No. 8,969,014 to Nordlund. The disclosures of Martinez-Molina and Nordlund are incorporated herein by reference in their entirety as the assay methods to which the SWATH-MS is applied are described there in detail.

In an alternative aspect, rather than an unbiased determination of compositions using SWATH-MS, a more selective biased determination can be employed when it is already known which proteins would be of greatest interest. This method is the SRM-MS method described above which permits selective measurement for identified proteins. Further, if desired, subsequent to application of SWATH-MS to identify suitable candidates, follow-up studies can be done using SRM-MS.

Thus, in one aspect, the invention is directed to a multiplexed method to identify and quantify proteins to which a test compound binds in a sample containing numerous proteins which method comprises thermal shift assays conducted as described in these above-referenced documents as well as further described in the present application and applying SWATH-MS or SRM-MS to analyze the results. The invention also is directed to identifying compounds that bind a target protein.

In some embodiments, the sample is a cell lysate. In addition in some embodiments, the method is performed by contacting the test compound with a living cell followed by lysing the cell to obtain the mixture of proteins to be analyzed according to the invention. In another formulation, the method comprises contacting a complex mixture with a test compound subjecting the sample to at least one temperature at which a target protein is more soluble when bound to a ligand and less soluble when not bound to a ligand, separating the fractions and determining the presence or amount of both targeted and non-targeted proteins in the sample by SWATH-MS or SRM-MS.

BRIEF DESCRIPTION OF THE DRAWINGS

FIG. 1 is a depiction from the prior art of the concept of SWATH-MS analysis. As a complex sample is subjected to chromatographic separation, each fraction is subjected to MS analysis in increments of small ranges of molecular weights such as 25 Da and the fractionation characteristic of the peptides or proteins in each of these intervals is assessed by mass spectrometry. For each of the sequence of determinations which is illustrated by the grey bar in FIG. 1, the protein composition as determined by mass spectrometry gives typical results as indicated in FIG. 2A-B. Each fraction from the chromatographic separation is surveyed over the spectrum of possible molecular weights, thus eliminating the bias otherwise present in a standard shotgun MS technique.

FIG. 2A shows the signature for peptides obtained by trypsin digestion as the fragmentation pattern, and FIG. 2B shows, for two exemplary peptides obtained from DHFR, the results actually obtained, and the expected signature is shown below the line in each case.

FIG. 3B shows that a protein to which P218 does not bind do not change $T_m$ in the presence of P218 as compared to its absence.

MODES OF CARRYING OUT THE INVENTION

Thermal shift assays for binding of compounds to proteins are based on the principle that when bound to a ligand, a protein is to some extent stabilized. Specifically it becomes more stable with respect to increased temperature-induced denaturation. Thus, a plot of the concentration of an unbound protein in solution as the temperature rises will show an inflection point at which the transition temperature between solubilized protein and insoluble protein ($T_m$) is at a relatively lower temperature than is found in the presence of a ligand that binds and thus stabilizes the protein. A typical such curve for DHFR in the presence and absence of methotrexate shows that in the absence of methotrexate, the solubility of DHFR decreases rapidly beginning around 40° C. and the curve has something of an inflection point at 45° C. In contrast, in the presence of methotrexate, depending on the concentration, the $T_m$ increases to about 56° C. for 10 µM methotrexate and to about 61° C. for 100 µM methotrexate. Since the curves for differing concentrations of ligand are different, one could use an isothermal determination in the region where the curves differ depending on the methotrexate concentration, in this case at about 59° C. to determine the affinity of the protein for the ligand. A typical such depiction shows this variation in stability as a function of methotrexate concentration.

It would be much more efficient if, instead of measuring the effect of a ligand on one protein at a time, it would be possible simultaneously to determine the binding ability of a ligand or test compound to a multiplicity of proteins at once without deciding in advance which protein to test or without using what is described above as "shotgun" MS which results in the biasing of results by virtue of the settings on the mass spectrometer—either the mass spectrometer is instructed to measure the fragmentation pattern from the most prevalent peptides in a digest, or to measure the fragmentation patterns of peptides of a particular molecular weight. The present invention provides a method whereby the thermal shift assays can be carried out in a conventional manner, but rather than relying on conventional setting of the mass spectrometer, a technique for scanning multiple molecular weight intervals in particular fractions generated in the chromatographic separation used to provide peptide units to the mass spec, the entire library of peptides is evaluated in light of a library of stored data. In order to do this effectively, it is necessary to provide these comparison data to which the fragmentation patterns generated can be compared, which requires a library of fragmentation patterns generated from peptides of the proteins present in the sample. This may include an entire proteome of an organism.

While all of the compounds tested to date of which applicants are aware increase the stability of the proteins with which they interact, thus enhancing their solubility and increasing their melting temperature, it is theoretically possible that a compound will be found that actually destabilizes a protein with which it interacts. In that case, the parameters will be reversed; the solubility of the protein at a given temperature will be decreased and the melting temperature will be lower. The assay would then be adjusted accordingly in terms of its interpretation.

The present inventors have conducted multiplexed CTSA with respect to >97% of the proteome for *M. tuberculosis* and 99.9% of the human and mouse proteomes and greater than 90% for rat, bovine and rabbit proteomes. Applicants often refer to mixtures containing "numerous" different proteins. By "numerous" is meant thousands of such proteins including the proteins described in such proteomes. By increasing the efficacy of this method, it is possible to identify and quantify which proteins in a mixture containing numerous proteins in fact bind to a test compound or conversely to identify a test compound that binds to a protein contained in a mixture including in such identification verification that it does or does not bind to additional proteins in the mixture.

In more detail, in one embodiment, the method of the invention is a multiplexed method to both identify and quantify proteins to which a test compound binds in the sample containing numerous proteins or to identify a compound that binds a target protein or target protein plus additional proteins quantitatively in a sample containing numerous proteins. The method comprises, in one alternative: (a) subjecting a first portion of a sample comprising numerous proteins that contains test compound and a second portion of the sample that does not contain test compound to at least one temperature at which at least some of the proteins in said sample are more soluble when bound to the test compound and less soluble when not bound to said test compound; (b) separating each of said first and second portions to obtain a soluble fraction and an insoluble fraction of each; (c) determining the concentration of a multiplicity of proteins in either the soluble fraction or the insoluble fraction of each portion or both; wherein said determining is performed in an unbiased manner by SWATH-MS or in a biased manner using SRM-MS. A protein whose concentration in the soluble fraction of the first portion is increased at said temperature as compared to the second portion and/or whose concentration in the insoluble fraction of the first portion is decreased at said temperature as compared to the second portion is identified as a protein that binds the test compound or conversely the compound is confirmed to bind to the protein.

An alternative method to determine these interactions is by: (a) subjecting a first portion of the sample that contains test compound and a second portion of the sample that does not contain test compound or aliquots thereof to a series of different temperatures, including a temperature which is equal to or greater than the initial melting temperature of at least some of the proteins in said sample; (b) separating each of said first and second portions or each aliquot to obtain a soluble and insoluble fraction; (c) determining the concentration of a multiplicity of proteins in either the soluble fraction or the insoluble fraction or aliquot of each portion or both; wherein the determining is performed in an unbiased manner by SWATH-MS or in a biased manner using SRM-MS wherein a protein whose concentration is maintained in the soluble fraction of said first portion or aliquot thereof at a higher temperature as compared to the soluble fraction of the second portion or aliquot thereof and/or whose concentration is decreased at a higher temperature in the insoluble fraction of said first portion or aliquot thereof as compared to the second portion or aliquot thereof is identified as a protein that binds said test compound or conversely that the test compound binds to this protein.

In an alternative manner to determine these interactions, the method comprises determining the inflection melting temperatures ($T_m$'s) of a multiplicity of proteins in a first portion of the sample that contains test compound; and determining the $T_m$'s of said multiplicity of proteins in a second portion of the sample that does not contain test compound and/or ascertaining $T_m$ values of said multiplicity of proteins in unbound form from stored or literature values; wherein said determining is performed in an unbiased manner by SWATH-MS or biased manner without the need for affinity reagents by SRM-MS; wherein a protein that exhibits a higher $T_m$ in the first portion as compared to the second portion or as compared to the stored or literature value is identified as a protein that binds to said test compound or conversely the compound is identified as binding said protein.

Utilizing an unbiased assay method such as SWATH-MS as a readout for thermal shift assay, the unbiased determination of proteome wide changes will permit the identification of new compound to protein interactions that will allow the discovery of potential new compound targets. In addition, this unbiased assay method such as SWATH-MS as a readout for thermal shift assay will allow the investigation of identifying new protein interactions with known and approved drugs for repurposing efforts. Finally, the unbiased assay method such as SWATH-MS as a readout for thermal shift assay of proteome wide changes will also identify novel networks of proteins perturbed by the interaction of a compound and a protein or proteins in the proteome identifying new protein targets upstream or downstream of the identified compound target that can also be targeted to enhance the action of a compound and its effect on a cell or organism.

Thus, the procedures generally described in the art for the thermal shift assay, including those based on cellular extracts can be markedly improved by analyzing the results using the SWATH-MS technique and using comparison to the proteome libraries for the organisms referenced above. This leads to greatly improved and more efficient method of drug testing as it is possible to determine not only whether a ligand binds to a desired target but also to analyze alternative proteins in the proteome for binding to the same ligand thus permitting evaluation of possible side effects of the test compound.

There are a number of ways that the thermal shift assay can be conducted. For a given sample, a series of temperatures over which it is likely that the melting curves of proteins will be found—i.e., between 40° C. and 80° C. can be obtained and multiple readouts of concentration of each protein in the soluble or insoluble fraction sample as a function of temperature can be employed. A change in the melting curve, e.g., a determination of $T_m$ for each protein could then be obtained and the results evaluated in a manner similar to that set forth in Example 1 below.

In a more abbreviated form, an arbitrary temperature can be chosen where proteins in general exhibit differential solubility and the amounts of each protein in the soluble or insoluble fraction could be determined. If the quantity of a protein increases in the soluble portion in the presence of the ligand or test compound, this is evidence of binding of the test compound to the protein. Because SWATH-MS permits this evaluation to be done in an unbiased manner for each protein in the proteome, both intended targets and other proteins can be included in the sample. Alternatively in a biased manner, SRM analysis of predefined proteins can be quantified without the need for additional quantitation reagents such as protein specific antibodies or chemical labels as needed in Western Blot analysis or Tandem Mass Tag approaches.

Alternatively, the amount of a particular protein in the soluble fraction as compared to the insoluble fraction can be compared at temperatures at which a protein is known to undergo at least partial denaturation.

In general, the temperatures measured are in the range of 40-80° C. as most proteins contain changes in solubility in this range. However, for individual proteins whose characteristics are known to be such that they denature only at higher temperatures or lower temperatures, an adjustment to the appropriate temperatures at which measurements can be taken would be evident to the skilled artisan.

The following example is offered to illustrate but not to limit the invention.

Example 1

Determination of Binding of P218 to DHFR

Figure 1:
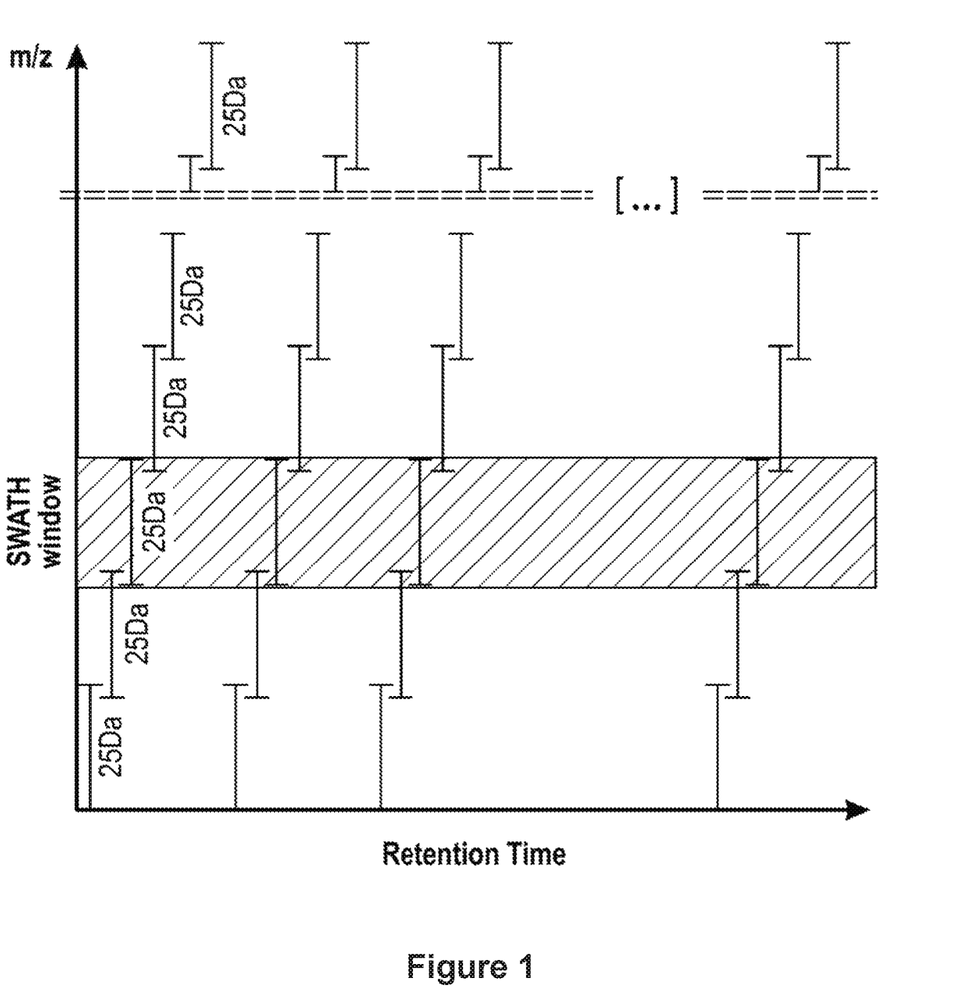
Figure 2A:
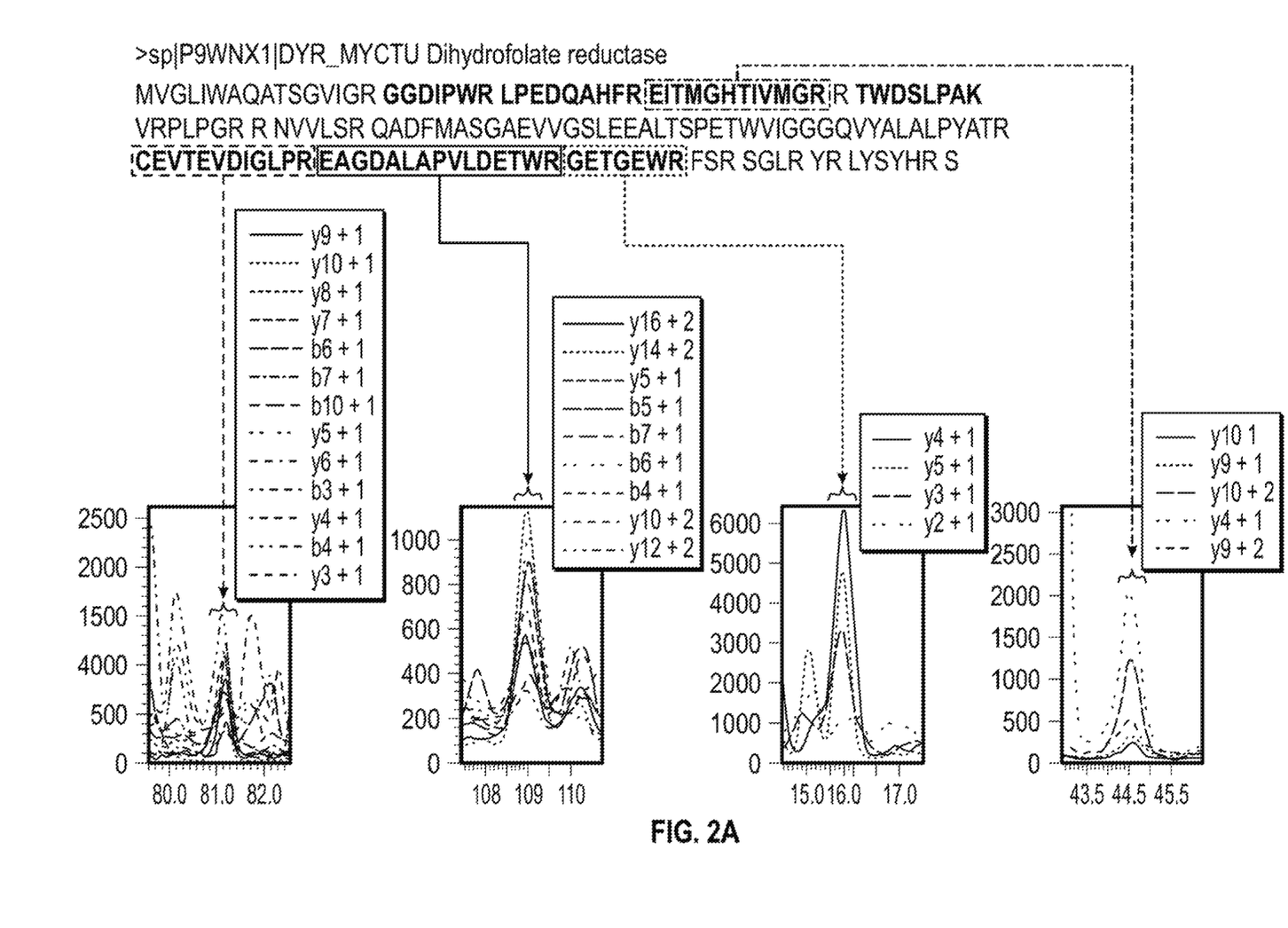
FIG. 2A-B show patterns obtained when a specific protein, dihydrofolate reductase (DHFR) is analyzed.
Figure 2B:
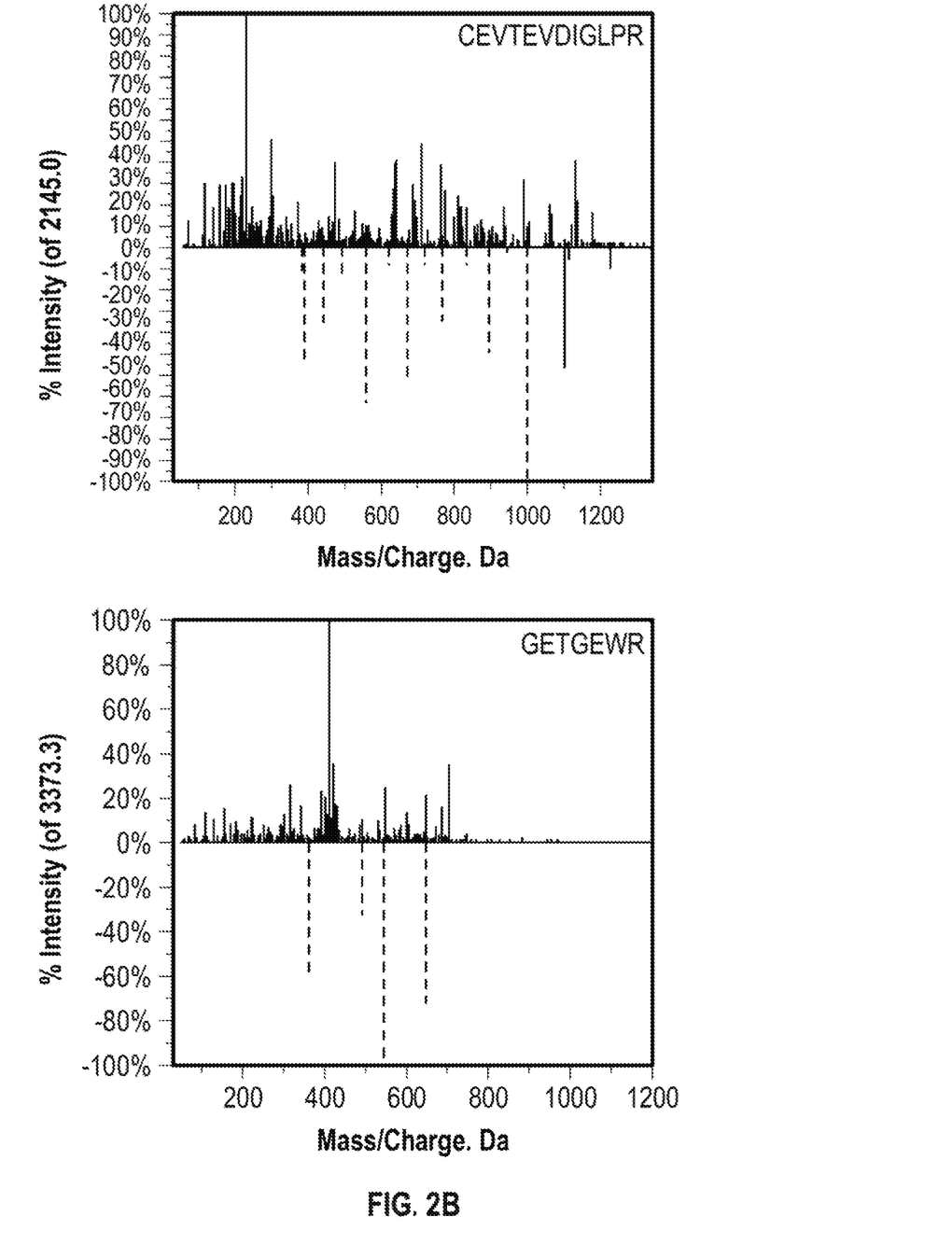

Lysates were prepared from *M. tuberculosis*. Lysates exposed to 150 nM of P218 were compared to lysates that were not treated with this compound. P218 is known to bind to DHFR which was used as an illustrative target protein. Portions of each lysate (with and without P218) were subjected to a series of four temperatures at 47° C., 53° C., 59° C. and 62° C. The portions were centrifuged to obtain precipitated protein and supernatant fractions which supernatant fractions were treated with trypsin and then subjected to liquid chromatography and mass spectrometry analysis using SWATH-MS. Based on an extensive peptide fragment library that covers more than 97% of the *M. tuberculosis* proteome, the results were analyzed to ascertain the concentrations of peptides derived from DHFR by proteolysis. The DHFR data in the library are based on analysis of purified DHFR similarly treated with the results shown for specific peptide fragments in FIGS. 2A and 2B.

Figure 3A:
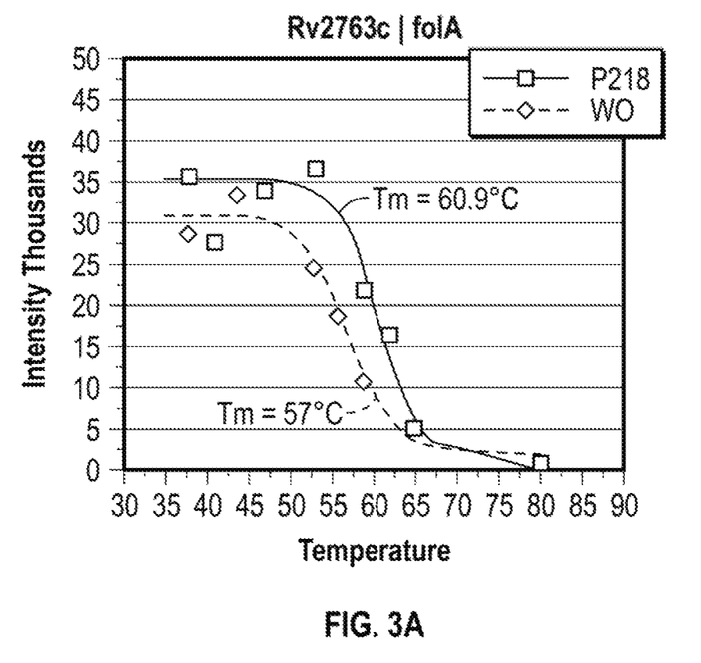
FIG. 3A-B show determinations of the inflection temperatures ($T_m$) for DHFR (Rv2763c) in the presence and absence of its known binding compound P218 is shown in FIG. 3A.

Based on matching this library to the results obtained with the treated and untreated lysate, the results shown in FIG. 3A were obtained. As shown in FIG. 3A, untreated samples showed a diminution of DHFR concentration between 47° C. and 53° C. which was not present in the samples treated with P218 wherein the concentration of DHFR was maintained at almost the same value at 53° C. as compared to 47° C.

Thus, this assay confirms that the method of the invention demonstrates the known binding ability of P218 for DHFR.

In more detailed experiments, conducted in a similar manner, melting curves were constructed in the presence and absence of P218. As shown in FIG. 3A, in the presence of P218, DHFR remained soluble at higher temperatures having a temperature at the inflection point ($T_m$) of 60.9° C. However, when P218 is absent, as shown in FIG. 3A, the $T_m$ of DHFR is 57° C. Thus, in the presence of P218, DHFR remains soluble up to a higher temperature.

Figure 3B:
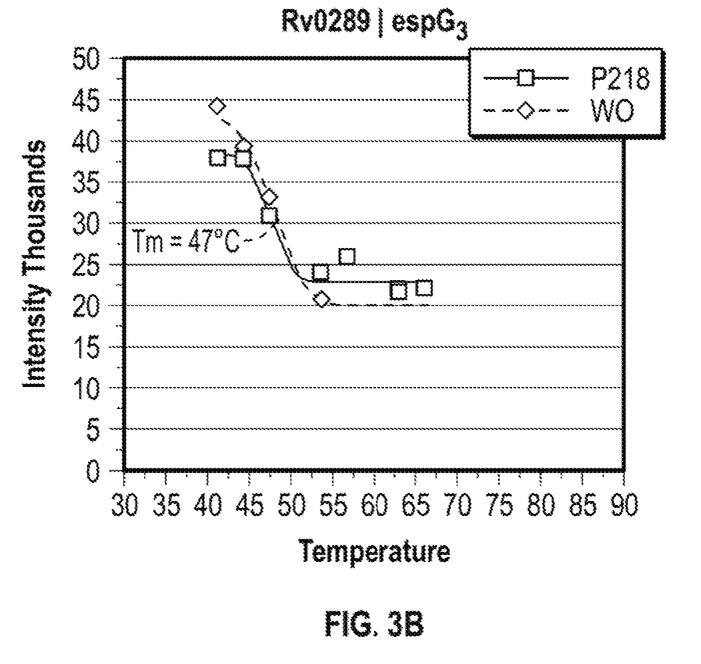

In contrast, a "non-target" protein, Rv0289/EspG3 (FIG. 3B) which is known not to bind P218 shows no difference in the $T_m$ values in the presence and absence of this compound.

Additional Embodiments

As noted above, there is a theoretic possibility that instead of stabilizing a protein to which it is bound, a compound may destabilize it. Rather than provide detailed claims for such a speculative possibility, applicants present below a depiction of how the same method could be applied in the case of such destabilization. In this case, the claims might read as follows: A multiplexed method to identify proteins to which a test compound binds in a sample containing numerous proteins or for identifying a compound capable of binding to a target protein contained in a sample comprising numerous proteins, including said target protein, which method comprises:

(a) subjecting a first portion of the sample that contains test compound and a second portion of the sample that does not contain test compound to at least one temperature at which at least some of the proteins in said sample are less soluble when bound to the test compound and more soluble when not bound to said test compound;

(b) separating each of said first and second portions to obtain a soluble fraction and an insoluble fraction of each;

(c) determining the concentration of a multiplicity of proteins in either the soluble fraction or the insoluble fraction of each portion or both;

wherein said determining is performed in an unbiased manner by Sequential Windowed data independent Acquisition of the Total High resolution Mass Spectroscopy (SWATH-MS); or wherein said determining is performed in a biased manner by Selected Reaction Monitoring (SRM-MS);

wherein a protein whose concentration in the soluble fraction of the first portion is decreased at said temperature as compared to the soluble fraction of the second portion and/or whose concentration in the insoluble fraction of the first portion is increased at said temperature as compared to the insoluble fraction of the second portion is identified as a protein that binds said test compound, or wherein a lower concentration of said target protein in the soluble fraction of the first portion at said temperature as compared to the soluble fraction of the second portion and/or a higher concentration of target protein in the insoluble fraction in the first portion at said temperature as compared to the insoluble fraction of the second portion identifies said test compound as binding the target protein.

An alternative test would be: A multiplexed method to identify proteins to which a test compound binds in a sample containing numerous proteins or for identifying a compound capable of binding to a target protein contained in a sample comprising numerous proteins, including said target protein, wherein at least some of said proteins are less soluble when bound to a test compound which method comprises:

(a) subjecting a first portion of the sample that contains a test compound and a second portion of the sample that does not contain test compound or aliquots thereof to a series of different temperatures, including a temperature which is equal to or less than the initial melting temperature of at least some of the proteins in said sample;

(b) separating each of said first and second portions or each aliquot thereof to obtain a soluble and insoluble fraction;

(c) determining the concentration of a multiplicity of proteins in either the soluble fraction or the insoluble fraction of each portion or both;

wherein said determining is performed in an unbiased manner by SWATH-MS; or wherein said determining is performed in a biased manner by SRM-MS;

wherein a protein whose concentration is maintained in the soluble fraction of said first portion or aliquots thereof at a lower temperature as compared to the soluble fraction of the second portion or aliquots thereof and/or whose concentration in the insoluble fraction of said first portion or aliquots thereof is increased at a higher temperature as compared to the insoluble portion of the second portion or aliquots thereof is identified as a protein that binds said test compound, or wherein when the concentration of said target protein is maintained in the soluble fraction of the first portion or aliquots thereof at a lower temperature as compared to the soluble fraction of the second portion or aliquots thereof and/or when the concentration of target protein in the insoluble fraction of said first portion or aliquots thereof is increased at a higher temperature than in the insoluble fraction of the second portion or aliquots thereof the test compound is identified as binding said target protein.

Still another alternative would be: A multiplexed method to identify proteins to which a test compound binds in a sample containing numerous proteins or for identifying a compound capable of binding to a target protein contained in a sample comprising numerous proteins, including said target protein, wherein at least some of said proteins are less stable when bound to a test compound which method comprises:

(a) determining the inflection melting temperatures ($T_m$'s) of a multiplicity of proteins in a first portion of the sample that contains test compound; and (b) determining the $T_m$'s of said multiplicity of proteins in a second portion of the sample that does not contain test compound and/or ascertaining $T_m$ values of said multiplicity of proteins in unbound form from stored or literature values;

wherein said determining is performed in an unbiased manner by SWATH-MS; or wherein said determining is performed in a biased manner by SRM-MS;

wherein a protein that exhibits a lower $T_m$ in the first portion as compared to the second portion or as compared to the stored or literature value is identified as a protein that binds to said test compound, or wherein when said target protein exhibits a lower $T_m$ in the first potion as compared to the second portion or as compared to the stored or literature value of said protein, the test compound is identified as binding the target protein.

Still another alternative would be: An improved method of determining whether a sample containing a multiplicity of proteins contains a target protein bound to a ligand of interest comprising the steps of:

(a) exposing the sample to a temperature which is capable of causing or enhancing precipitation of unbound protein to a lesser extent than it is capable of causing or enhancing precipitation of protein bound to the ligand;

(b) separating soluble from insoluble protein in the product of step a); and (c) analyzing either or both the soluble and insoluble protein fractions of step b) for the amount of said protein, wherein a protein whose concentration in the soluble fraction at said temperature is decreased in the presence as opposed to the absence of the test compound, or whose concentration in the insoluble fraction is increased in the presence as opposed to the absence of the test compound, is identified as a protein that binds said test compound, wherein the improvement comprises analyzing said fraction(s) in an unbiased manner by SWATH-MS. or wherein the improvement comprises analyzing said fraction(s) in a biased manner by SRM-MS.

In all these cases, cell lysates from live or collected cells could be used as the sample.

The invention claimed is:

1. A multiplexed method to identify proteins to which a test compound binds in a sample containing numerous proteins or for identifying a compound capable of binding to a target protein contained in a sample comprising numerous proteins, including said target protein, which method comprises:

(a) subjecting a first portion of the sample that contains test compound and a second portion of the sample that does not contain test compound to at least one temperature at which at least some of the proteins in said sample are more soluble when bound to the test compound and less soluble when not bound to said test compound;

(b) separating each of said first and second portions to obtain a soluble fraction and an insoluble fraction of each;

(c) determining the concentration of a multiplicity of proteins in either the soluble fraction or the insoluble fraction of each portion or both;

wherein said determining is performed in an unbiased manner by Sequential Windowed data independent Acquisition of the Total High resolution Mass Spectroscopy (SWATH-MS); or wherein said determining is performed in a biased manner by Selected Reaction Monitoring (SRM-MS);

wherein a protein whose concentration in the soluble fraction of the first portion is increased at said temperature as compared to the soluble fraction of the second portion and/or whose concentration in the insoluble fraction of the first portion is decreased at said temperature as compared to the insoluble fraction of the second portion is identified as a protein that binds said test compound, or wherein a higher concentration of said target protein in the soluble fraction of the first portion at said temperature as compared to the soluble fraction of the second portion and/or a lower concentration of target protein in the insoluble fraction in the first portion at said temperature as compared to the insoluble fraction of the second portion identifies said test compound as binding the target protein.

2. The method of claim 1 wherein the sample is a cell lysate.

3. The method of claim 2 wherein the lysate is of cells from human, mouse, rat, bovine, rabbit, *E. coli* or *M. tuberculosis*.

4. The method of claim 1 wherein said sample comprises living cells and said cells are lysed prior to step (a).

5. An improved method of determining whether a sample containing a multiplicity of proteins contains a target protein bound to a ligand of interest comprising the steps of:

(a) exposing the sample to a temperature which is capable of causing or enhancing precipitation of unbound protein to a greater extent than it is capable of causing or enhancing precipitation of protein bound to the ligand;

(b) separating soluble from insoluble protein in the product of step a); and (c) analyzing either or both the soluble and insoluble protein fractions of step b) for the amount of said protein, wherein a protein whose concentration in the soluble fraction at said temperature is increased in the presence as opposed to the absence of the test compound, or whose concentration in the insoluble fraction is decreased in the presence as opposed to the absence of the test compound, is identified as a protein that binds said test compound, wherein the improvement comprises analyzing said fraction(s) in an unbiased manner by SWATH-MS, or wherein the improvement comprises analyzing said fraction(s) in a biased manner by SRM-MS.

6. The method of claim 5 wherein said sample contains numerous proteins and the presence of more than one of said proteins is determined.

7. The method of claim 5 wherein the sample is a cell lysate.

8. The method of claim 7 wherein the lysate is of cells from species such as human, mouse, rat, bovine, rabbit, *E. coli* or *M. tuberculosis*.

9. The method of claim 5 wherein said sample comprises living cells and said cells are lysed prior to step (a).

10. A method for identifying proteins of living cells to which a test compound binds, comprising the steps of:

(a) contacting a portion of said living cells with the test compound;

(b) subjecting the living cells to lysis conditions to generate a first sample and subjecting said living cells that have not been contacted with said compound to lysis conditions to generate a second sample;

(c) subjecting said first sample and said second sample to at least one temperature at which at least some of the proteins in said sample are more soluble when bound to the test compound and less soluble when not bound to said test compound;
(d) separating each of said first and second samples to obtain a soluble fraction and an insoluble fraction of each;
(e) determining the concentration of a multiplicity of proteins in either the soluble fraction or the insoluble fraction of each sample or both;
wherein said determining is performed in an unbiased manner by SWATH-MS; or
wherein said determining is performed in a biased manner by SRM-MS;
wherein any protein whose concentration in the soluble fraction of the first sample is increased at said temperature as compared to soluble fraction of the second sample and/or whose concentration in the insoluble fraction of the first sample is decreased at said temperature as compared to the insoluble portion of the second sample
is identified as a protein that binds said test compound.

\* \* \* \* \*